United States Patent [19]

Odenwälder et al.

[11] Patent Number: 5,702,877
[45] Date of Patent: Dec. 30, 1997

[54] COLOR PHOTOGRAPHIC SILVER HALIDE MATERIAL

[75] Inventors: Heinrich Odenwälder, Leverkusen; Hans Langen, Bonn; Uwe Dahlhaus, Burscheid; Heinz-Dieter Schütz, Leverkusen, all of Germany

[73] Assignee: Agfa-Gevaert AG, Germany

[21] Appl. No.: 605,475

[22] Filed: Feb. 26, 1996

[30] Foreign Application Priority Data

Mar. 7, 1995 [DE] Germany ............... 195 07 913.2

[51] Int. Cl.⁶ .................................................. G03C 7/32
[52] U.S. Cl. ........................ 430/551; 430/544; 430/554; 430/555; 430/611; 430/613
[58] Field of Search ...................... 430/551, 544, 430/554, 555, 611–613

[56] References Cited

U.S. PATENT DOCUMENTS

| Re. 31,893 | 5/1985 | Sugita et al. | 430/555 |
|---|---|---|---|
| 4,268,592 | 5/1981 | Tschopp | 430/555 |
| 4,451,557 | 5/1984 | Lok et al. | 430/551 |
| 4,526,863 | 7/1985 | Mihayashi et al. | 430/555 |
| 4,923,790 | 5/1990 | Kato et al. | 430/551 |
| 4,954,431 | 9/1990 | Nishijima et al. | 430/555 |
| 4,968,597 | 11/1990 | Suda et al. | 430/551 |
| 5,116,723 | 5/1992 | Kajiwara et al. | 430/551 |
| 5,158,864 | 10/1992 | Matejec et al. | 430/551 |
| 5,262,292 | 11/1993 | Krishnamurthy et al. | 430/555 |
| 5,441,851 | 8/1995 | Singer et al. | 430/372 |

FOREIGN PATENT DOCUMENTS

| 442017 | 1/1969 | Japan | 430/554 |
|---|---|---|---|
| 4172446 | 6/1992 | Japan | 430/544 |

*Primary Examiner*—Thorl Chea
*Attorney, Agent, or Firm*—Connolly & Hutz

[57] ABSTRACT

A colour photographic silver halide material with a support, at least one silver halide emulsion layer and at least one non-light sensitive layer applied thereto, wherein the silver halide emulsion layer contains at least one colour coupler, and wherein the silver halide emulsion layer or the non-light sensitive layer contains a compound of the formula (I)

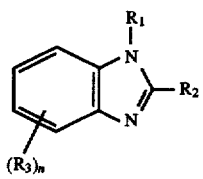

in which $R_1$, $R_2$ and $R_3$ mean hydrogen or an organic residue and n means 0 or an integer from 1 to 4 or $R_1$ and $R_2$ together, $R_1$ and an adjacent residue $R_3$ together or two adjacent residues $R_3$ together form a carbocyclic or heterocyclic ring with 5 to 7 ring atoms or $R_1$, $R_2$ or $R_3$ mean a bridging member by means of which two compounds of the formula (I) are attached together or $R_1$, $R_2$ or $R_3$ are attached to a polymer via a bridging member, wherein at least one of the substituents $R_1$, $R_2$ and $R_3$ is an organic residue, is distinguished by improved grain.

14 Claims, No Drawings

COLOR PHOTOGRAPHIC SILVER HALIDE MATERIAL

This invention relates to a colour photographic silver halide material with improved grain.

Colour photographic materials, in particular colour films, should have the lowest possible grain. However, since they should simultaneously have elevated photosensitivity and photosensitivity is conventionally increased by enlarging the silver halide grains, so in turn degrading grain, it is often not possible to produce fine-grained colour photographic materials of elevated sensitivity.

The object of the invention was to improve grain without loss of sensitivity.

It has now surprisingly been found that this object may be achieved by adding certain benzimidazoles.

The present invention thus provides a colour photographic silver halide material with a support, at least one silver halide emulsion layer and at least one non-light sensitive layer applied thereto, wherein the silver halide emulsion layer contains at least one colour coupler, and wherein the silvere halide emulsion layer or the non-light sensitive layer contains a compound of the formula (I)

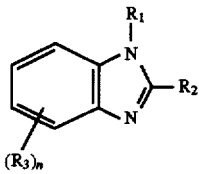

in which $R_1$, $R_2$ and $R_3$ mean hydrogen or an organic residue and n means 0 or an integer from 1 to 4 or $R_1$ and $R_2$ together, $R_1$ and an adjacent residue $R_3$ together or two adjacent residues $R_3$ together form a carbocyclic or heterocyclic ring with 5 to 7 ring atoms or $R_1$, $R_2$ or $R_3$ mean a bridging member by means of which two compounds of the formula (I) are attached together or $R_1$, $R_2$ or $R_3$ are attached to a polymer via a bridging member, wherein at least one of the substituents $R_1$, $R_2$ and $R_3$ is an organic residue.

$R_1$ preferably means hydrogen, optionally substituted saturated or unsaturated alkyl, cycloalkyl, aryl or hetaryl, $R_2$ preferably means hydrogen, optionally substituted saturated or unsaturated alkyl, cycloalkyl, aryl, hetaryl, —$SR_4$, $OR_4$ or $COR_4$, $R_3$ preferably means optionally substituted saturated or unsaturated alkyl, aryl, halogen, $OR_4$, $SR_4$, $COR_4$, $COOR_4$, $CONHR_4$, NH acyl, $SO_2R_4$ or CN and $R_4$ preferably means optionally substituted saturated or unsaturated alkyl, cycloalkyl, aryl or hetaryl.

$R_1$ particularly preferably means hydrogen, unsubstituted alkyl with 1 to 20 C atoms or alkyl with 1 to 4 C atoms substituted by hydroxy, phenyl, alkylmercapto or arylmercapto, $R_2$ particularly preferably means saturated or unsaturated alkyl with 1 to 20 C atoms, alkyl with 1 to 4 C atoms substituted by alkylmercapto, cyano, alkoxycarbonyl or S—$R_4$, $R_3$ particularly preferably means alkyl with 1 to 20 C atoms, phenyl or halogen, $R_4$ particularly preferably means alkyl with 1 to 20 C atoms and n particularly preferably means 0, 1 or 2.

If n means>1, the substituents $R_3$ may be identical or different.

The compound of the formula (I) is in particular used in the silver halide emulsion layer concerned in a quantity of 50 to 500 mg/m$^2$ of material.

The compound of the formula (I) is preferably dissolved or dispersed together with the colour coupler in a high-boiling organic solvent; the solution or dispersion is then emulsified in an aqueous binder solution, conventionally in an aqueous gelatine solution.

The compound of the formula (I) is preferably used together with a 2-equivalent magenta coupler of the pyrazolone series of a molecular weight of between 500 and 1500 used in a quantity of 0.5 to 1.5 g/m$^2$.

Preferred pyrazolone couplers are of the formula (II)

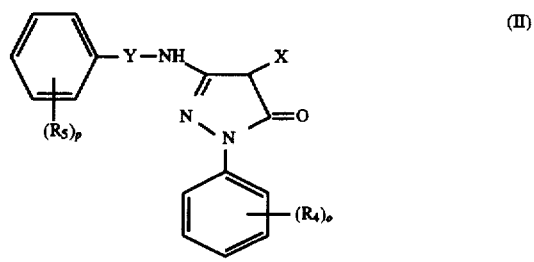

in which $R_4$ means a substituent from the group comprising halogen, CN, alkylsulphonyl, arylsulphonyl, sulphamoyl, sulphamido, carbamoyl, carbonamido, alkoxy, acyloxy, aryloxy, alkoxycarbonyl, ureido, nitro, alkyl and trifluoromethyl, $R_5$ means a substituent such as $R_4$ or aryl, alkylsulphoxyl, arylsulphoxyl, acyl, imido, carbamato, heteroacylyl, alkylthio, carboxyl or hydroxyl, X means an elimination group, Y means a direct bond or CO and o and p mean 0 or a number from 1 to 5, wherein, should o and/or p be>1, the substituents $R_4$ or $R_5$ may be identical or different.

Preferred elimination groups are halogen, alkoxy, aryloxy, alkylthio, arylthio, acyloxy, sulphonamido, sulphonyloxy, carbonamido, arylazo, imido, nitrogenous heterocyclic residues and hetarylthio residues.

Particularly preferred magenta couplers are of the formula (III)

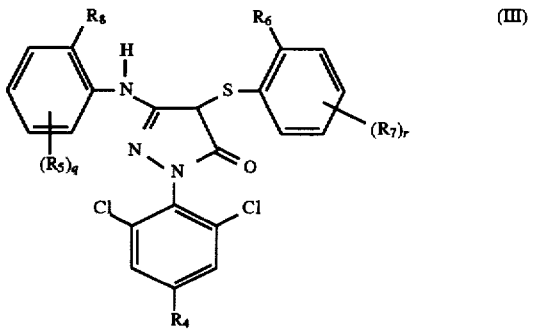

in which $R_4$ and $R_5$ have the above-stated meaning $R_6$ means acylamino or sulphonylamino, $R_7$ means hydrogen or an organic residue, in particular hydrogen, $R_8$ means chlorine or $C_1$–$C_4$ alkoxy, r and q mutually independently mean 0, 1 or 2.

Suitable compounds of the formula I are:

| No. | $R_1$ | $R_2$ | $R_3$ |
|---|---|---|---|
| 1 | H | $C_{17}H_{33}$ | H |
| 2 | H | $C_{13}H_{27}$ | H |
| 3 | H | $C_{13}H_{27}$ | 4,6-dimethyl |
| 4 | H | $C_{17}H_{31}$ | H |
| 5 | benzyl | $CH_2$-S-$C_{12}H_{25}$ | H |
| 6 | $CH_3$ | $SCH_2CH_2CN$ | 5-$C_{14}H_{27}O$ |
| 7 | H | $C_6H_{13}S$ | H |
| 8 | H | $C_8H_{17}S$ | H |
| 9 | H | $C_{10}H_{21}S$ | H |
| 10 | H | $C_{12}H_{25}S$ | H |
| 11 | H | $C_{13}H_{27}S$ | H |
| 12 | H | $C_{14}H_{29}S$ | H |
| 13 | H | $C_{16}H_{33}S$ | H |
| 14 | H | $C_{18}H_{37}S$ | H |
| 15 | H | $CH(CH_3)CO_2C_{12}H_{25}$ | H |
| 16 | H | $C_{13}H_{27}$ | $C_4H_9S$ |
| 17 | H | $CH_2CH_{25}C_{18}H_{37}$ | H |
| 18 | H | $CH_2SC_{12}H_{25}$ | H |
| 19 | $CH_3$ | $SC_{12}H_{25}$ | 5,6-dichloro |
| 20 | $C_2H_5$ | $SC_{12}H_{25}$ | H |
| 21 | $C_{12}H_{25}$ | H | H |
| 22 | $CH_2OH$ | $C_{13}H_{27}$ | H |
| 23 | $CH_2SC_{12}H_{25}$ | $C_{13}H_{27}$ | H |
| 24 | $CH_2SC_{12}H_{25}$ | $SC_2H_5$ | 5-$OCH_3$ |
| 25 | $CH_3$ | $SC_{10}H_{21}$ | 5-OH |
| 26 | $CH_3$ | $SC_{10}H_{21}$ | 5-$OCOCH_3$ |
| 27 | H | $SC_{12}H_{25}$ | 5-CN |
| 28 | H | 4-$C_4H_9O$-phenyl | 5-$CH_3CO$ |
| 29 | H | 4-cylohexenyl | 5-$NHSO_2C_{16}H_{33}$ |
| 30 | H | 2-$C_{10}H_{21}S$-phenyl | H |

Further suitable compounds of the formula I are:

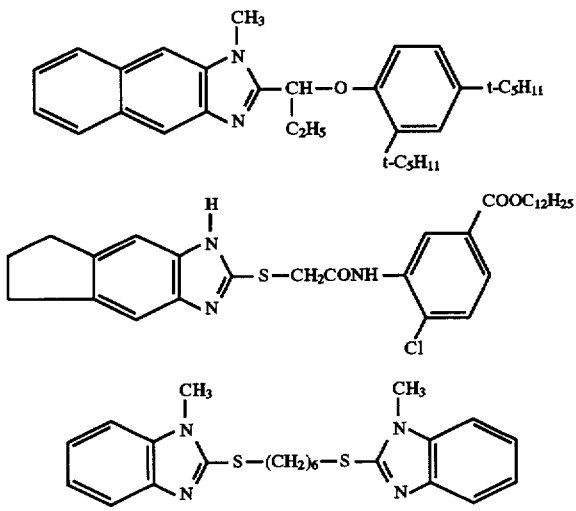

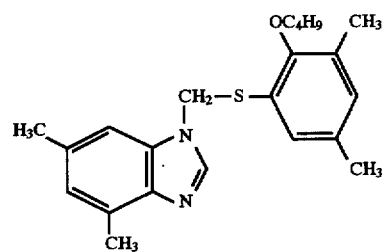

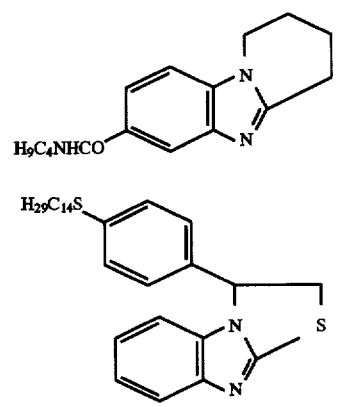

The compounds according to the invention may be prepared using known methods, for example *Methoden der Organischen Chemie*, volume E8c, *Hetarene* III/part 3, Thieme Verlag 1994.

The preparation of compound 10 is stated by way of example:

160.9 g of 2-mercaptobenzimidazole are dissolved in mixture of
500 ml of methanol and
200 ml Na methylate solution (30 wt. %).
247.8 ml of 1-chlorodecane (95 wt. %) are stirred in within 1 hour. The mixture is refluxed for 4 hours, cooled to 40 to 45° C. and combined with
1000 ml of water. The precipitate is filtered out, washed with
2000 ml of water, filtered out, stirred for 30 minutes in
1000 ml of acetonitrile, filtered out, washed with
1000 ml of acetonitrile and dried.

Yield: 269 g (85% of theoretical) of colourless crystals; melting point 97°–98° C.

Suitable couplers of the formulae (II) and (III) are:

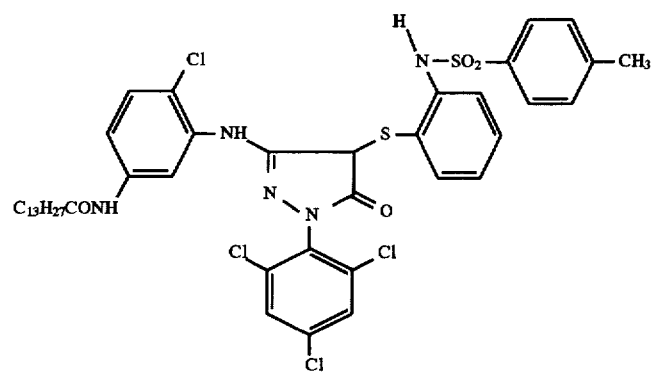
II-1
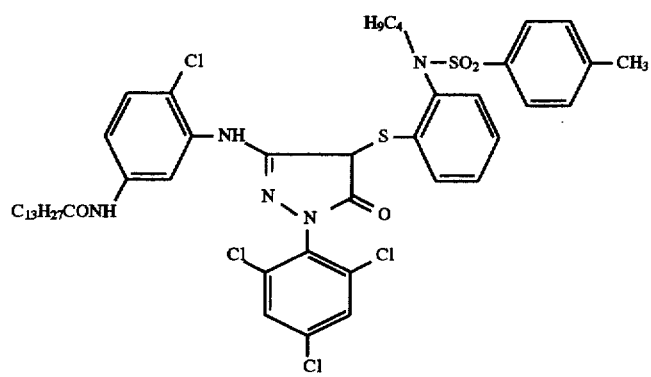
II-2
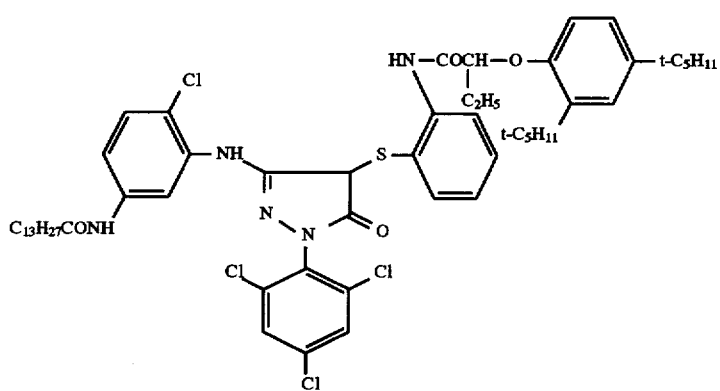
II-3
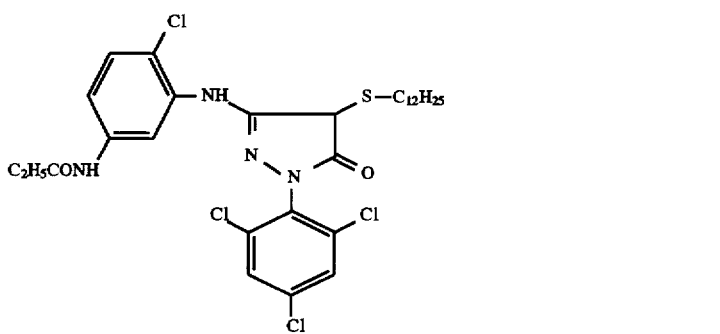
II-4

-continued
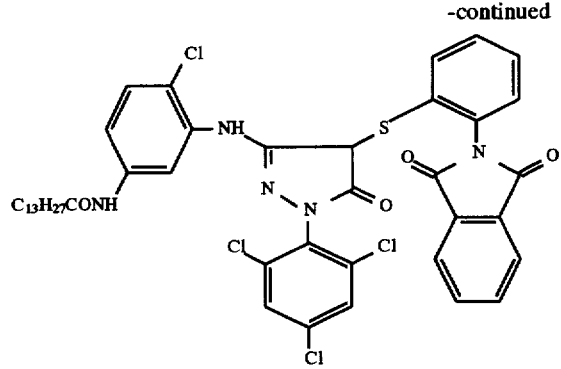
II-5
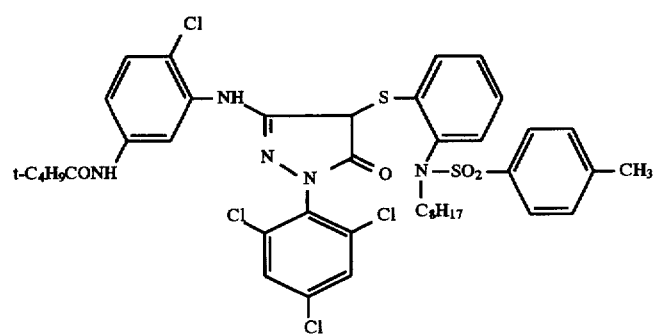
II-6
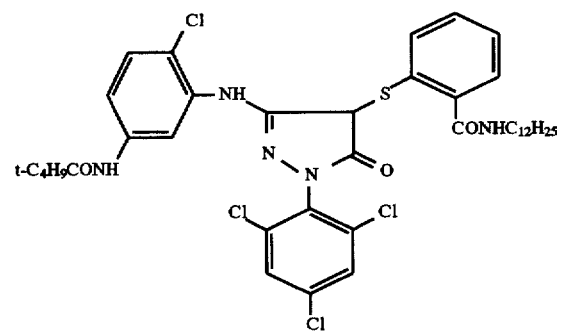
II-7
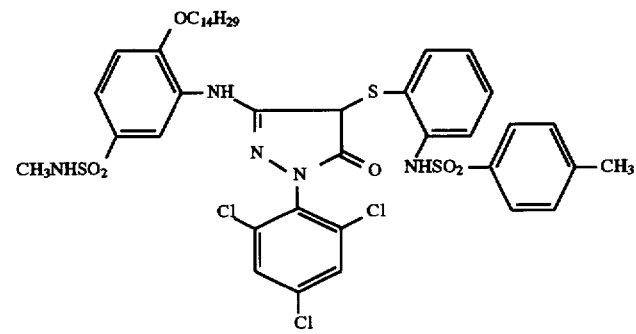
II-8

-continued

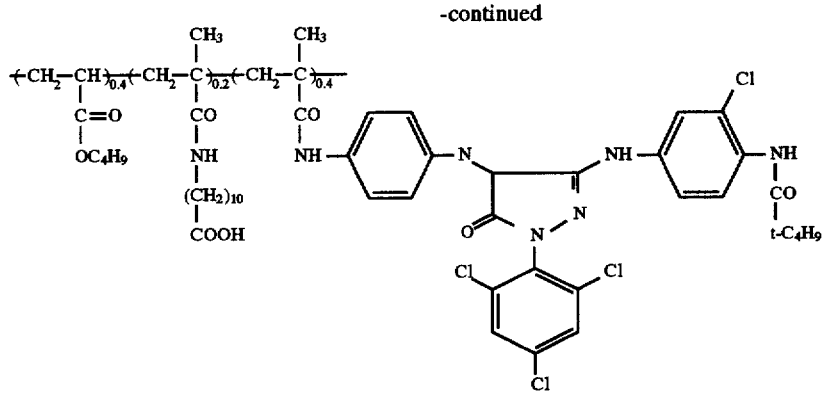
II-9

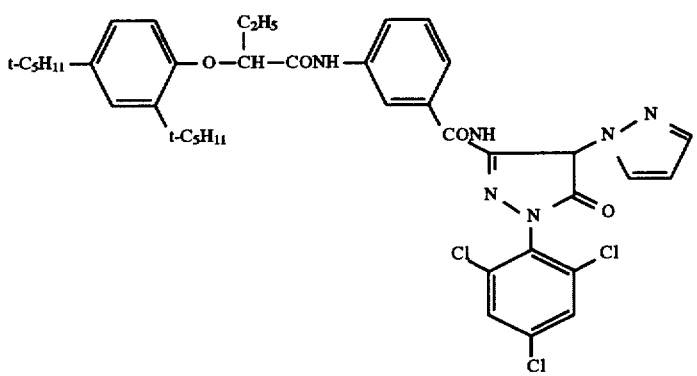
II-10

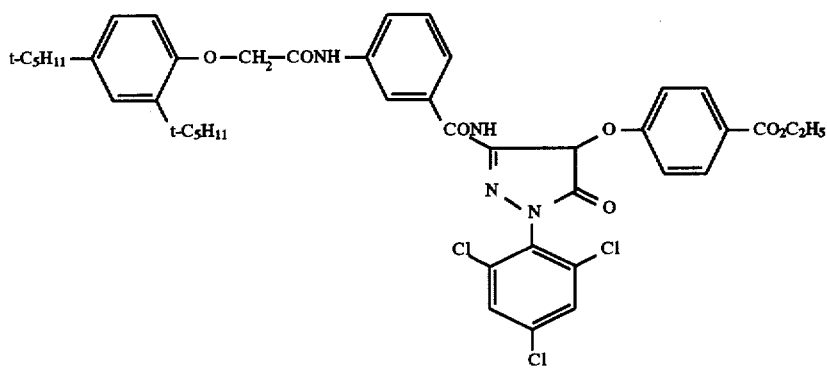
II-11

The compounds according to the invention of the formula I may also be used in combination with yellow or cyan couplers and improve the sensitivity/grain ratio in these cases too.

The material according to the invention is in particular a colour photographic silver halide material with a support, at least one red-sensitive silver halide emulsion layer containing at least one cyan coupler, at least one green-sensitive silver halide emulsion layer containing at least one magenta coupler, at least one blue-sensitive silver halide emulsion layer containing at least one yellow coupler, wherein all the green-sensitive and all the red-sensitive silver halide emulsion layers are arranged closer to the support than all the blue-sensitive silver halide emulsion layers. A yellow filter layer is conventionally located between the blue-sensitive silver halide emulsion layers on the one hand and the green-sensitive and red-sensitive silver halide emulsion layers on the other hand. This filter layer may contain as its active constituent colloidal silver or a yellow dye which it must be possible to decolour or rinse out. Such dyes are known from the literature.

The material preferably contains 2 or 3 blue-, green- and red-sensitive layers.

Suitable transparent supports for the production of colour photographic materials are, for example, films and sheet of semi-synthetic and synthetic polymers, such as cellulose nitrate, cellulose acetate, cellulose butyrate, polystyrene, polyvinyl chloride, polyethylene terephthalate, polyethylene naphthalate and polycarbonate. These supports may also be coloured black for light-shielding purposes. The surface of the support is generally subjected to a treatment in order to improve the adhesion of the photographic emulsion layer, for example corona discharge with subsequent application of a substrate layer. The reverse side of the support may be provided with a magnetic layer and an antistatic layer.

The essential constituents of the photographic emulsion layers are the binder, silver halide grains and colour couplers.

Gelatine is preferably used as the binder. Gelatine may, however, be entirely or partially replaced with other synthetic, semi-synthetic or also naturally occurring polymers. Synthetic gelatine substitutes are, for example, polyvinyl alcohol, poly-N-vinyl pyrrolidone, polyacryl-amides, polyacrylic acid and the derivatives thereof, in particular the copolymers thereof. Naturally occurring gelatine substitutes are, for example, other proteins such as albumin or casein, cellulose, sugar, starch or alginates. Semi-synthetic gelatine substitutes are usually modified natural products. Cellulose derivatives such as hydroxyalkyl cellulose, carboxymethyl cellulose and phthalyl cellulose together with gelatine derivatives obtained by reaction with alkylating or acylating agents or by grafting polymerisable monomers, are examples of such products.

The binders should have a sufficient quantity of functional groups available so that satisfactorily resistant layers may be produced by reaction with suitable hardeners. Such functional groups are in particular amino groups, but also carboxyl groups, hydroxyl groups and active methylene groups.

The silver halide present as the photosensitive constituent in the photographic material may contain chloride, bromide or iodide or mixtures thereof as the halide. For example, the halide content of at least one layer may consist of 0 to 15 mol. % of iodide, 0 to 20 mol. % of chloride and 65 to 100 mol. % of bromide. The silver halide crystals may be predominantly compact, for example regularly cubic or octahedral, or they may have transitional shapes: Preferably, however, lamellar crystals may also be present, the average ratio of diameter to thickness of which is preferably at least 5:1, wherein the diameter of a grain is defined as the diameter of a circle the contents of which correspond to the projected surface area of the grain. The layers may, however, also have tabular silver halide crystals in which the ratio of diameter to thickness is substantially greater than 5:1, for example 10 12:1 to 30:1.

The silver halide grains may also have a multi-layered grain structure, in the simplest case with one internal zone and one external zone of the grain (core/shell), wherein the halide composition and/or other modifications, such as for example doping, of the individual grain zones are different. The average grain size of the emulsions is preferably between 0.2 µm and 2.0 µm, the grain size distribution may be both homodisperse and heterodisperse. A homodisperse grain size distribution means that 95% of the grains deviate by no more than ±30% from the average grain size. The emulsions may, in addition to the silver halide, also contain organic silver salts, for example silver benzotriazolate or silver behenate.

Two or more types of silver halide emulsions which are produced separately may be used as a mixture.

The silver halides are precipitated, deionised, chemically ripened, spectrally sensitised and stabilised in the conventional manner.

The differently sensitised emulsion layers are associated with non-diffusing monomeric or polymeric colour couplers which may be located in the same layer or in an adjacent layer. Usually, cyan couplers are associated with the red-sensitive layers, magenta couplers with the green-sensitive layers and yellow couplers with the blue-sensitive layers.

Colour couplers to produce the cyan partial colour image are generally couplers of the phenol or α-naphthol type.

Colour couplers to produce the magenta partial colour image are generally couplers of the pyrazolone or pyrazolotriazole type.

Colour couplers to produce the yellow partial colour image are generally couplers of the acylacetanilide and malonamide type.

The colour couplers may be 4-equivalent couplers, but they may also be 2-equivalent couplers. The latter are differentiated from 4-equivalent couplers by containing a substituent at the coupling site which is eliminated on coupling. 2-equivalent couplers are considered to be those which are colourless, as well as those which have an intense intrinsic colour which on colour coupling disappears or is replaced by the colour of the image dye produced (masking couplers), and white couplers which, on reaction with colour developer oxidation products, give rise to substantially colourless products. 2-equivalent couplers are further considered to be those which contain an eliminable residue at the coupling site, which residue is liberated on reaction with colour developer oxidation products and so either directly or after one or more further groups are eliminated from the initially eliminated residue (for example, DE-A-27 03 145, DE-A-28 55 697, DE-A-31 05 026, DE-A-33 19 428), produces a specific desired photographic effect, for example as a development inhibitor or accelerator. Examples of such 2-equivalent couplers are the known DIR couplers as well as DAR or FAR couplers.

DIR couplers which release azole type development inhibitors, for example triazoles and benzotriazoles, are described in DE-A-24 14 006, 26 10 546, 26 59 417, 27 54 281, 28 42 063, 36 26 219, 36 30 564, 36 36 824, 36 44 416. Further advantages for colour reproduction, i.e. colour separation and colour purity, and for the reproduction of detail, i.e. sharpness and grain, are to be achieved with such DIR, couplers, which, for example, do not release the development inhibitor immediately as a consequence of coupling with an oxidised colour developer, but instead only after a further subsequent reaction, which is, for example, achieved with a time control group. Examples of this are described in DE-A-28 55 697, 32 99 671, 38 18 231, 35 18 797, in EP-A-0 157 146 and 0 204 175, in U.S. Pat. No. 4,146,396 and 4,438,393 and in GB-A-2 072 363.

DIR couplers which release a development inhibitor which is decomposed in the developer bath to substantially photographically inactive products are, for example, described in DE-A-32 09 486 and EP-A-0 167 168 and 0 219 713. By this means, unproblematic development and processing consistency are achieved.

When DIR couplers are used, particularly those which eliminate a readily diffusible development inhibitor, improvements in colour reproduction, for example more differentiated colour reproduction, may be achieved by suitable measures during optical sensitisation, as are described, for example, in EP-A-0 115 304, 0 167 173, GB-A-2 165 058, DE-A-37 00 419 and U.S. Pat. No. 4,707,436.

The DIR couplers may, in a multi-layer photographic material, be added to the most various layers, for example also to non-photosensitive layers or interlayers. Preferably, however, they are added to the photosensitive silver halide emulsion layers, wherein the characteristic properties of the silver halide emulsion, for example its iodide content, the structure of the silver halide grains or the grain size distribution thereof influence the photographic properties achieved. The influence of the released inhibitors may, for example, be restricted by the incorporation of an inhibitor scavenging layer according to DE-A-24 31 223. For reasons of reactivity or stability, it may be advantageous to use a DIR coupler which on coupling forms a colour in the layer in which it is accommodated, which is different from the colour to be produced in this layer.

In order to increase sensitivity, contrast and maximum density, principally DAR or FAR couplers may be used which eliminate a development accelerator or fogging agent. Compounds of this type are described, for example, in DE-A-25 34 466, 32 09 110, 33 33 355, 34 10 616, 34 29 545, 34 41 823, in EP-A-0 089 834, 0 110 511, 0 118 087, 0 147 765 and in U.S. Pat. No. 4,618,572 and 4,656,123.

Reference is made to EP-A-193 389 as an example of the use of BAR couplers (bleach accelerator releasing couplers).

It may be advantageous to modify the effect of a photographically active group eliminated from a coupler by causing an intermolecular reaction of this group after its release with another group according to DE-A-35 06 805.

Since with the DIR, DAR or FAR couplers it is mainly the activity of the residue released on coupling that is desired and the chromogenic properties of these couplers are of lesser importance, those DIR, DAR or FAR couplers which give rise to substantially colourless products on coupling are also suitable (DE-A-15 47 640).

The eliminable residue may also be a ballast residue such that, on reaction with colour developer oxidation products, coupling products are obtained which are diffusible or have at least weak or restricted mobility (U.S. Pat. No. 4,420,556).

The material may, in addition to couplers, contain various compounds which, for example, may liberate a development inhibitor, a development accelerator, a bleach accelerator, a developer, a silver halide solvent, a fogging agent or an anti-fogging agent, for example so-called DIR, hydroquinones and other compounds as, for example, described in U.S. Pat. Nos. 4,636,546, 4,345,024, 4,684,604 and in DE-A-31 45 640, 25 15 213, 24 47 079 and in EP-A-198 438. These compounds fulfil the same function as the DIR, DAR or FAR couplers, except that they produce no coupling products.

High-molecular weight colour couplers are, for example, described in DE-C-1297 417, DE-A-24 07 569, DE-A-31 48 125, DE-A-32 17 200, DE-A-33 20 079, DE-A-33 24 932, DE-A-33 31 743, DE-A-33 40 376, EP-A-27,284, U.S. Pat. No. 4,080,211. The high-molecular weight colour couplers are generally produced by polymerisation of ethylenically unsaturated monomeric colour couplers. They may, however, also be obtained by polyaddition or polycondensation.

The incorporation of couplers or other compounds into the silver halide emulsion layers may proceed by initially producing a solution, dispersion or emulsion of the compound concerned and then adding it to the pouring solution for the layer concerned. Selection of the appropriate solvent or dispersant depends on the particular solubility of the compound.

Methods for the introduction of compounds which are substantially insoluble in water by a grinding process are described, for example, in DE-A-26 09 741 and DE-A-26 09 742.

Hydrophobic compounds may also be introduced into the pouring solution by using high-boiling solvents, so-called oil formers. Corresponding methods are described, for example, in U.S. Pat. No. 2,322,027, U.S. Pat. No. 2,801,170, U.S. Pat. No. 2,801,171 and EP-A-0 043 037.

Oligomers or polymers, so-called polymeric oil formers, may be used instead of high-boiling solvents.

The compounds may also be introduced into the pouring solution in the form of filled latices. Reference is, for example, made to DE-A-25 41 230, DE-A-25 41 274, DE-A-28 35 856, EP-A-0 014 921, EP-A-0 069 671, EP-A-0 130 115, U.S Pat. No. 4,291,113.

The non-diffusible inclusion of anionic water-soluble compounds (for example of dyes) may also proceed with the assistance of cationic polymers, so-called mordanting polymers.

Suitable oil formers are, for example, phthalic acid alkyl esters, phosphoric acid esters, phosphoric acid esters, citric acid esters, benzoic acid esters, amides, fatty acid esters, trimesic acid esters, alcohols, phenols, aniline derivatives and hydrocarbons.

Examples of suitable oil formers are dibutyl phthalate, dicyclohexyl phthalate, di-2-ethylhexyl phthalate, decyl phthalate, triphenyl phosphate, tricresyl phosphate, 2-ethylhexyldiphenyl phosphate, tricyclohexyl phosphate, tri-2-ethylhexyl phosphate, tridecyl phosphate, tributoxyethyl phosphate, trichloropropyl phosphate, di-2-ethylhexylphenyl phosphate, 2-ethylhexyl benzoate, dodecyl benzoate, 2-ethylhexyl p-hydroxybenzoate, diethyldodecanamide, N-tetradecylpyrrolidone, isostearyl alcohol, 2,4-di-t-amylphenol, dioctyl acelate, glycerol tributyrate, iso-stearyl lactate, trioctyl citrate, N,N-dibutyl-2-butoxy-5-t-octyl aniline, paraffin, dodecylbenzene and diisopropylnaphthalene.

The non-photosensitive interlayers generally arranged between layers of different spectral sensitivity may contain agents which prevent an undesirable diffusion of developer oxidation products from one photosensitive layer into another photosensitive layer with a different spectral sensitisation.

Suitable agents, which are also known as scavengers or DOP scavengers, are described in Research Disclosure 17 643 (December 1978), section VII, 17 842 (February 1979) and 18 716 (November 1979), page 650 and in EP-A-0 069 070, 0 098 072, 0 124 877, 0 125 522.

If there are two or more partial layers of the same spectral sensitisation, then they may differ in composition, particularly in terms of the type and quantity of silver halide grains. In general, the partial layer with the greater sensitivity will be located further from the support than the partial layer with lower sensitivity. Partial layers of the same spectral sensitisation may be adjacent to each other or may be separated by other layers, for example by layers of different spectral sensitisation. Thus, for example, all high sensitivity and all low sensitivity layers may be grouped together each in a package of layers (DE-A-19 58 709, DE-A-25 30 645, DE-A-26 22 922).

The photographic material may also contain UV light absorbing compounds, optical whiteners, spacers, filter dyes, formalin scavengers, light stabilisers, antioxidants, $D_{min}$ dyes, additives to improve stabilisation of dyes, couplers and whites and to reduce colour fogging, plasticisers (latices), biocides and others.

Ultra-violet absorbing couplers (such as cyan couplers of the α-naphthol type) and ultra-violet absorbing polymers may also be used. These ultra-violet absorbents may be fixed into a specific layer by mordanting.

Filter dyes suitable for visible light include oxonol dyes, hemioxonol dyes, styryl dyes, merocyanine dyes, cyanine dyes and azo dyes. Of these dyes, oxonol dyes, hemioxonol dyes and merocyanine dyes are particularly advantageously used.

Suitable optical whiteners are, for example, described in Research Disclosure 17 643 (December 1978), section V, in U.S. Pat. Nos. 2,632,701, 3,269,840 and in GB-A-852 075 and 1 319 763.

Certain binder layers, in particular the layer furthest away from the support, but also occasionally interlayers, particularly if they constitute the layer furthest away from the support during manufacture, may contain photographically inert particles of an inorganic or organic nature, for example as flatting agents or spacers (DE-A-33 31 542, DE-A-34 24 893, Research Disclosure 17 643 (December 1978), section XVI).

The average particle diameter of the spacers is in particular in the range from 0.2 to 10 μm. The spacers are insoluble in water and may be soluble or insoluble in alkali, wherein alkali-soluble spacers are generally removed from the photographic material in the alkaline developing bath. Examples of suitable polymers are polymethyl methacrylate, copolymers of acrylic acid and methyl methacrylate together with hydroxypropylmethyl-cellulose hexahydrophthalate.

Additives to improve the stability of dyes, couplers and whites and to reduce colour fogging (*Research Disclosure* 17 643 (December 1978), section VII) may belong to the following classes of chemical substances: hydroquinones, 6-hydroxychromans, 5-hydroxycoumarans, spirochromans, spiroindans, p-alkoxyphenols, sterically hindered phenols, gallic acid derivatives, methylene dioxybenzenes, aminophenols, sterically hindered mines, derivatives with esterified or esterified phenolic hydroxyl groups, metal complexes.

Compounds having both a sterically hindered amine partial structure and a sterically hindered phenol partial structure in a single molecule (U.S. Pat. No. 4,268,593) are particularly effective in preventing the impairment of yellow colour images as a consequence of the action of heat, moisture and light. Spiroindans (JP-A-159 644/81) and chromans which are substituted by hydroquinone diethers or monoethers (JP-A-89 835/80) are particularly effective in preventing the impairment of magenta colour images, in particular their impairment as a consequence of the action of light.

The layers of the photographic material according to the invention may be hardened with conventional hardeners. Suitable hardeners are, for example, formaldehyde, glutaraldehyde and similar aldehyde compounds, diacetyl, cyclopentadione and similar ketone compounds, bis-(2-chloroethylurea), 2-hydroxy-4,6-dichloro-1,3,5-triazine and other compounds containing reactive halogen (U.S. Pat. No. 3,288,775, U.S. Pat. No. 2,732,303, GB-A-974 723 and GB-A-1 167 207), divinylsulphone compounds, 5-acetyl-1, 3-diacryloylhexahydro-1,3,5-triazine and other compounds containing a reactive olefin bond (U.S. Pat. No. 3,635,718, U.S. Pat. No. 3,232,763 and GB-A-994 869); N-hydroxymethyl-phthalimide and other N-methylol compounds (U.S. Pat. No. 2,732,316 and U.S. Pat. No. 2,586, 168); isocyanates (U.S. Pat. No. 3,103,437); aziridine compounds (U.S. Pat. No. 3,017,280 and U.S. Pat. No. 2,983, 611); acid derivatives (U.S. Pat. No. 2,725,294 and U.S. Pat. No. 2,725,295); compounds of the carbodiimide type (U.S. Pat. No. 3,100,704); carbamoylpyridinium salts (DE-A-22 25 230 and DE-A-24 39 551); carbamoyloxypyridinium compounds (DE-A-24 08 814); compounds with a phosphorus-halogen bond (JP-A-113 929/83); N-carbonyloximide compounds (JP-A-43353/81); N-sulphonyloximido compounds (U.S. Pat. No. 4,111,926), dihydroquinoline compounds (U.S. Pat. No. 4,013,468), 2-sulphonyl-oxypyfidinium salts (JP-A-110 762/81), formamidinium salts (EP-A-0 162 308), compounds with two or more N-acyloximino groups (U.S. Pat. No. 4,052,373), epoxy compounds (U.S. Pat. No. 3,091,537), compounds of the isoxazole type (U.S. Pat. No. 3,321,313 and U.S. Pat. No. 3,543,292); halogen carboxyaldehydes, such as mucochloric acid; dioxane derivatives, such as dihydroxydioxane and dichlorodioxane; and inorganic hardeners such as chrome alum and zirconium sulphate.

Hardening may be effected in a known manner by adding the hardener to the pouring solution for the layer to hardened, or by overcoating the layer to be hardened with a layer containing a diffusible hardener.

There are included in the classes listed slow acting and fast acting hardeners as well as so-called instant hardeners, which are particularly advantageous. Instant hardeners are taken to be compounds which harden suitable binders in such a way that immediately after pouring, at the latest after 24 hours, preferably at the latest after 8 hours, hardening is concluded to such an extent that there is no further alteration in the sensitometry and swelling of the layered structure determined by the crosslinking reaction. Swelling is taken to be the difference between the wet layer thickness and the dry layer thickness during aqueous processing of the film (*Photogr. Sci. Eng.* 8 (1964), 275; *Photogr. Sci. Eng.* (1972), 449).

These hardeners which react very rapidly with gelatine are, for example, carbamoylpyridinium salts, which are capable of reacting with the free carboxyl groups of the gelatine, so that the latter react with free amino groups of the gelatine to form peptide bonds crosslinking the gelatine.

Colour photographic negative materials are conventionally processed by developing, bleaching, fixing and rinsing or by developing, bleaching, fixing and stabilising without subsequent rinsing, wherein bleaching and fixing may be combined into a single processing stage. Colour developer compounds which may be used are all developer compounds having the ability to react, in the form of their oxidation product, with colour couplers to form azomethine or indophenol dyes. Suitable colour developer compounds are aromatic compounds containing at least one primary amino group of the p-phenylenediamine type, for example N,N-dialkyl-p-pheneylenediamines such as N,N-diethyl-phphenylenediamine, 1-(N-ethyl-N-methanesulphonamido-ethyl)-3-methyl-p-phenylenediamine, 1-(N-ethyl-N-hydroxyethyl)-3-methyl-p-phenylenediamine and 1-(N-ethyl-N-methoxyethyl)-3-methyl-p-phenylenediamine. Further usable colour developers are, for example, described in *J. Amer. Chem. Soc.* 73, 3106. (1951) and G. Haist *Modern Photographic Processing*, 1979, John Wiley & Sons, New York, pages 545 et seq.

An acid stop bath or rinsing may follow after colour development.

Conventionally, the material is bleached and fixed immediately after colour development. Bleaches which may be used are, for example, Fe(III) salts and Fe(III) complex salts such as ferricyanides, dichromates, water soluble cobalt complexes. Iron(III) complexes of amino-polycarboxylic acids are particularly preferred, in particular for example complexes of ethylenediamine-tetraacetic acid, propylene-diaminetetraacetic acid, diethylenetriaminepentaacetic acid, nitrilotriacetic acid, iminodiacetic acid, N-hydroxyethylethylenediaminetriacetic acid, alkyliminodi-carboxylic acids and of corresponding phosphonic acids. Persulphates and peroxides, for example hydrogen peroxide, are also suitable as bleaches.

Rinsing usually follows the bleach/fixing bath or fixing bath, which is performed as countercurrent rinsing or comprises several tanks with their own water supply.

Favourable results may be obtained by using a subsequent finishing bath which contains no or only a little formaldehyde.

Rinsing may, however, be completely replaced with a stabilising bath, which is conventionally operated countercurrently. If formaldehyde is added, this stabilising bath also assumes the function of a finishing bath.

EXAMPLE 1 (COMPARISON)

A colour photographic recording material for colour negative development (layer structure 1A) was produced by applying the following layers in the stated sequence onto a transparent cellulose triacetate film base. The stated quantities relate in each case to 1 m$^2$. The corresponding quantities of AgNO$_3$ are stated for the quantity of silver halide applied; the silver halides are stabilised with 0.5 g of 4-hydroxy-6-methyl- 1,3,3 a,7-tetraazaindene per mol of AgNO$_3$.

| Layer 1 (Anti-halation layer) |
| --- |
| 0.12 g of dye FA 1 |
| 0.12 g of dye FA 2 |
| 0.8 g of gelatine |

| Layer 2 (low-sensitivity red-sensitive layer) |
| --- |
| 0.8 g AgNO$_3$ of a red-sensitised AgBrClI emulsion with 10.5 mol. % of chloride and 2.4 mol. % of iodide, average grain diameter 0.35 μm |
| 0.6 g of gelatine |
| 0.21 g of colourless coupler C1 |
| 0.01 g of DIR coupler D1 |
| 0.02 g of coloured coupler RC-1 |
| 0.01 g of coloured coupler YC-1 |
| 0.25 g of tricresyl phosphate (TCP) |

| Layer 3 (medium-sensitivity red-sensitive layer) |
| --- |
| 1.6 g AgNO$_3$ of a red-sensitised AgBrClI emulsion with 10.4 mol. % of chloride, 9.4 mol. % of iodide, average grain diameter 0.5 μm, |
| 0.8 g AgNO$_3$ of a red-sensitised AgBrI emulsion with 6.7 mol. % of iodide, average grain diameter 0.8 μm |
| 0.22 g of colourless coupler C1 |
| 0.07 g of coloured coupler RC-1 |
| 0.03 g of coloured coupler YC-1 |
| 0.04 g of DIR coupler D-1 |
| 0.9 g of gelatine |
| 0.32 g of TCP |

| Layer 4 (high-sensitivity red-sensitive layer) |
| --- |
| 1.6 g AgNO$_3$ of red-sensitised AgBrClI emulsion with 6.8 mol. % of iodide, average grain diameter 1.1 μm, |
| 1.2 g of gelatine |
| 0.15 g of colourless coupler C2 |
| 0.05 g of DIR coupler D2 |
| 0.20 g of TCP |

| Layer 5 (interlayer) |
| --- |
| 1.0 g of gelatine |
| 0.1 g of dye FA3 |

| Layer 6 (low-sensitivity green-sensitive layer) |
| --- |
| 0.54 g AgNO$_3$ of a green-sensitised AgBrClI emulsion with 10.4 mol. % of chloride, 9.5 mol. % of iodide, average grain diameter 0.5 μm |
| 0.9 g of gelatine |
| 0.43 g of colourless coupler II-1 |
| 0.005 g of DIR coupler D-1 |
| 0.001 g of DIR coupler D-3 |
| 0.02 g of coloured coupler YM-1 |
| 0.05 g of scavenger SC-1 |
| 0.46 g of TCP |

| Layer 7 (medium-sensitivity green-sensitive layer) |
| --- |
| 1.1 g AgNO$_3$ of a green-sensitive AgBrClI emulsion with 10.4 mol. % of chloride, 9.5 mol. % of iodide, average grain diameter 0.5 μm |
| 0.34 g AgNO$_3$ of a green-sensitive AgBrI emulsion with 6.7 mol. % of iodide, average grain diameter 0.7 μm |
| 0.24 g of colourless coupler II-1 |
| 0.04 g of coloured coupler YM-1 |
| 0.005 g of DIR coupler D1 |
| 0.003 g of DIR coupler D3 |
| 0.9 g of gelatine |
| 0.30 g of TCP |

| Layer 8 (high-sensitivity green-sensitive layer) |
| --- |
| 1.7 g AgNO$_3$ of a green-sensitised AgBrI emulsion with 6.8 mol. % of iodide, average grain diameter 1.1 μm |
| 1.2 g of gelatine |
| 0.2 g of colourless coupler II-4 |
| 0.05 g of coloured coupler YM-2 |
| 0.05 g of DIR coupler D2 |
| 0.3 g of TCP |

Layer 9 (interlayer)

| | |
|---|---|
| 0.4 g | of gelatine |
| 0.02 g | of polyvinylpyrrolidone |

Layer 10 (yellow filter layer)

| | |
|---|---|
| 0.1 g | of yellow colloidal silver |
| 0.2 g | of gelatine |
| 0.06 g | of scavenger SC1 |
| 0.2 g | of polyvinylpyrrolidone |
| 0.1 g | of TCP |

Layer 11 (low-sensitivity blue-sensitive layer)

| | |
|---|---|
| 0.18 g | $AgNO_3$ of a blue-sensitised AgBrClI emulsion with 15 mol. % of chloride, 9 mol. % of iodide, average grain diameter 0.78 μm |
| 0.2 g | $AgNO_3$ of a blue-sensitised AgBrClI emulsion with 10.4 mol. % of chloride, 9.5 mol. % of iodide, average grain diameter 0.5 μm |
| 0.89 g | $AgNO_3$ of a blue-sensitised AgBrClI emulsion with 10 mol. % of iodide, average grain diameter 1.15 μm |
| 1.0 g | of gelatine |
| 1.1 g | of colourless coupler Y-1 |
| 0.03 g | of DIR coupler D-1 |
| 1.1 g | of TCP |

Layer 12 (medium-sensitivity blue-sensitive layer)

| | |
|---|---|
| 0.12 g | $AgNO_3$ of a blue-sensitive AgBrClI emulsion with 15 mol. % of chloride, 8.8 mol. % of iodide, average grain diameter 0.77 μm |
| 0.28 g | $AgNO_3$ of a blue-sensitive AgBrClI emulsion with 15 mol. % of chloride, 12 mol. % of iodide, average grain diameter 1.0 μm |
| 0.77 g | of gelatine |
| 0.58 g | of colourless coupler Y-1 |
| 0.58 g | of TCP |

Layer 13 (high-sensitivity blue-sensitive layer)

| | |
|---|---|
| 16 g | $AgNO_3$ of a blue-sensitised AgBrI emulsion with 12 mol. % of iodide, average grain diameter 1.2 μm |
| 0.9 g | of gelatine |
| 0.1 g | of colourless coupler Y-1 |
| 0.02 g | of DIR coupler D-2 |
| 0.3 g | of UV absorber UV-2 |
| 0.2 g | of TCP |

Layer 14 (micrate layer)

| | |
|---|---|
| 0.3 g | $AgNO_3$ of an AgBrI emulsion with 4 mol. % of iodide, average grain diameter 0.05 μm |
| 1.4 g | of gelatine |
| 0.2 g | of UV absorber UV-1 |
| 0.3 g | of UV absorber UV-2 |
| 0.5 g | of TCP |

Layer 15 (protective and hardening layer)

| | |
|---|---|
| 0.2 g | of gelatine |
| 0.86 g | of hardener of the formula |

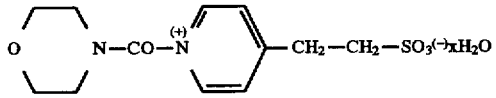

Substances used in example 1:

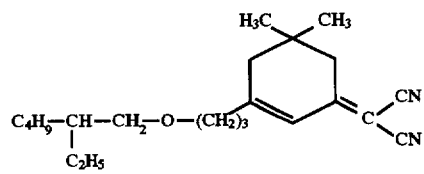

UV-1

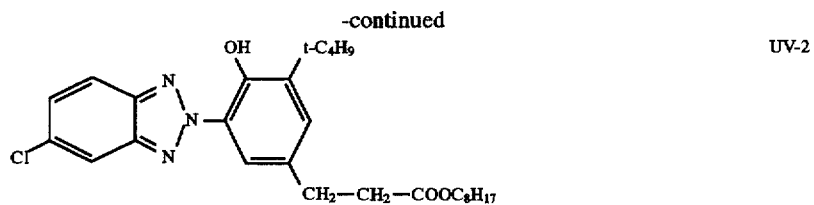
UV-2
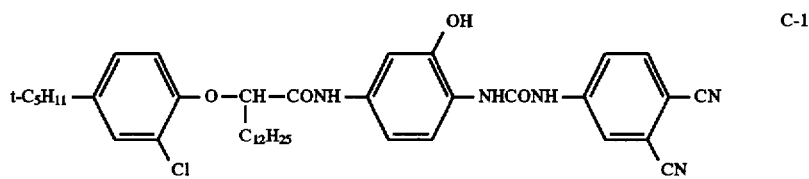
C-1
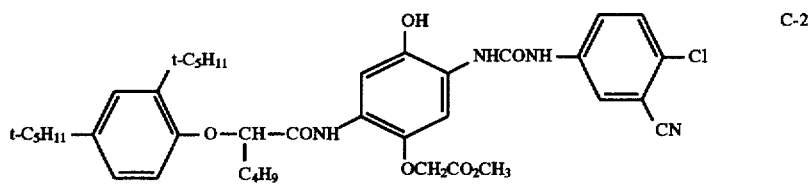
C-2
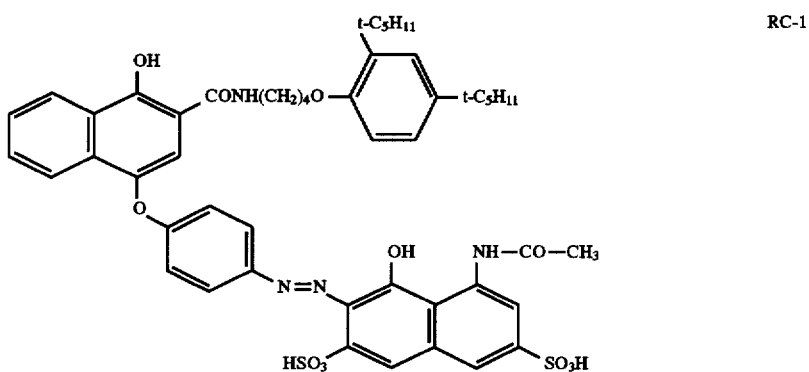
RC-1
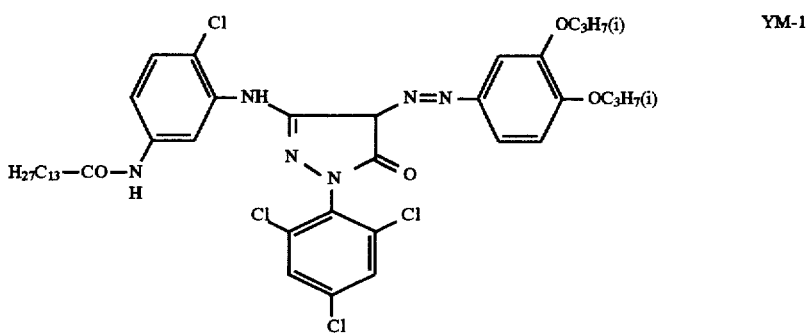
YM-1
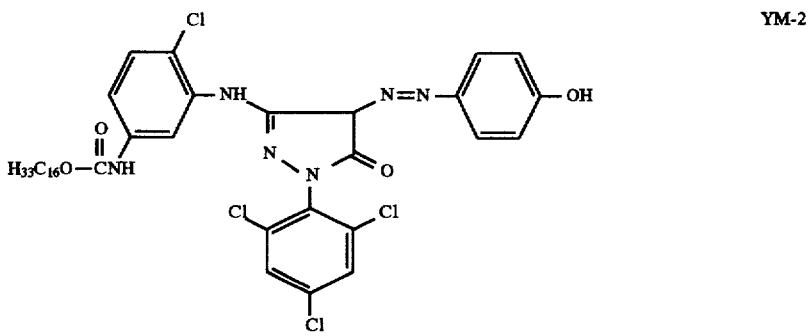
YM-2

Y-1
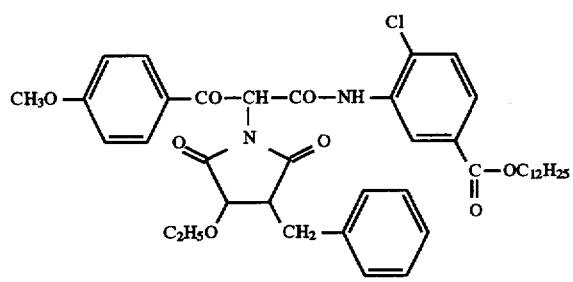
D-1
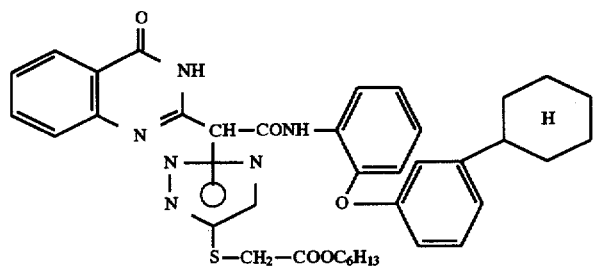
D-2
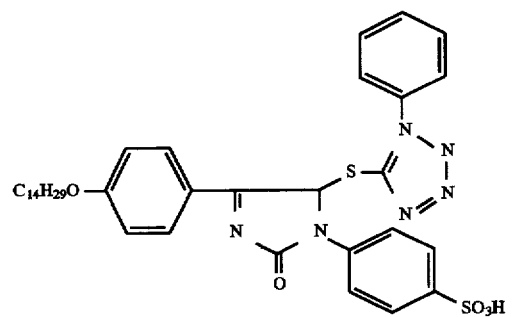
D-3
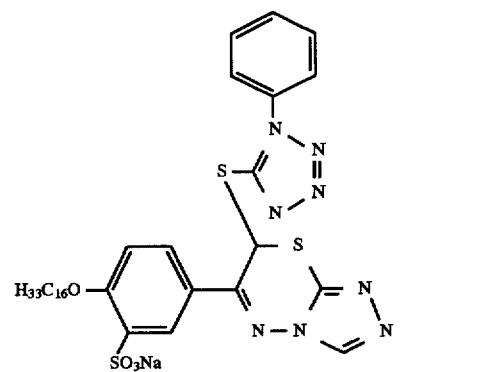

-continued

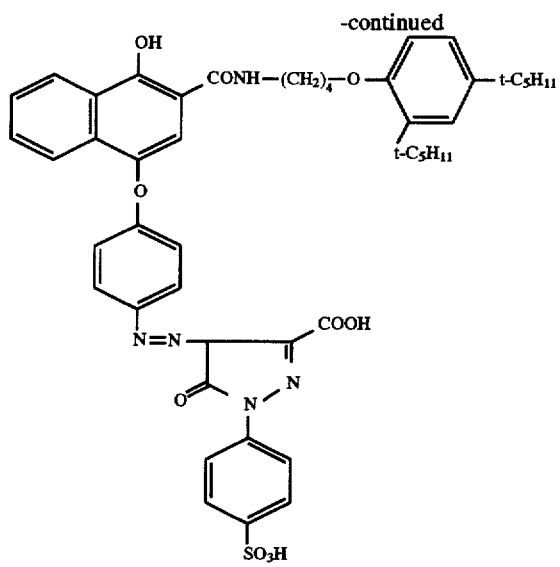

YC-1

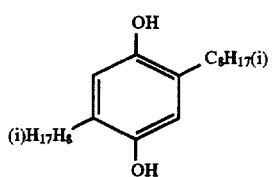

SC-1

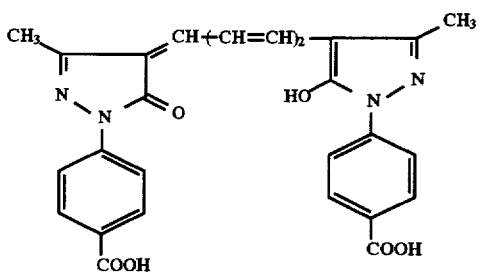

FA-1

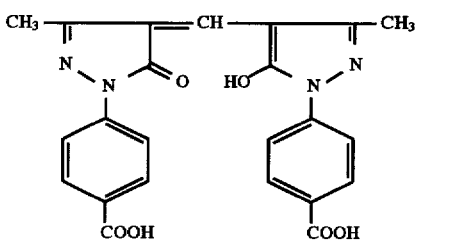

FA-2

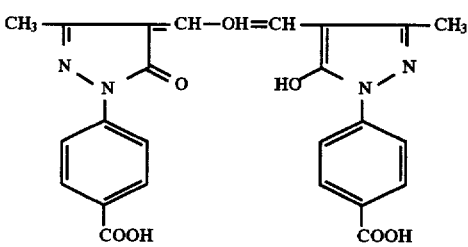

FA-3

Layer structure 1B (according to the invention) differs from 1A in that 100 mol. % of compound I-3, relative to the quantity of coupler in the layer concerned, were additionally emulsified into layers 3 and 4.

One sample of each of layer structures 1A and 1B was exposed with white light behind a grey step wedge (exposure time: 0.01 s) and processed using a colour negative process as described in The British Journal of Photography 1974, pages 597 and 598. RMS values (=root-mean-squares) were determined at various cyan colour densities as a measure of colour grain using a 48 μm diameter measuring aperture. The measurement method is described in: T. H. James, The Theory of the Photographic Process, 4th edition, MacMillan Publ. Co., New York (1977), page 619. Numerical values for both layer structures 1A and 1B are shown in table 1.

TABLE 1

| Structure | Cyan grain (RMS) at | | |
|---|---|---|---|
| | colour density 0.2 above fog | colour density 0.6 above fog | colour density 1.0 above fog |
| 1A | 17.0 | 12.8 | 11.1 |
| 1B | 14.8 | 11.1 | 9.5 |

The material according to the invention exhibits distinctly improved cyan grain.

EXAMPLE 2

Layer Structure 2A differs from 1A by 0.25 g/m² of black colloidal silver being used instead of the two dyes FA1 and FA2 in layer 1 (anti-halation layer), and 170 mg of dye FA4 in dispersed form being used in layer 10 instead of yellow colloidal silver and 200 mg of compound HM-1 being used instead of the hardener in layer 15. The further samples 2B–2L differ from 2A in that other magenta couplers and different stabilisers according to the invention were emulsified into the green-sensitive layers 6 and 7 in a quantity of 80 mol. % relative to the particular couplers. The ratios may be found in the following table 2.

Layer Structures 2B, 2D, 2F, 2H, 2J and 2L are according to the invention.

FA-4:

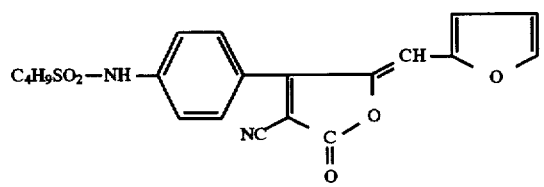

HM-1

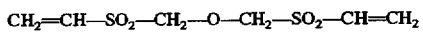

TABLE 2

| Structure | Magenta coupler in layer 6/m² | Magenta coupler in layer 7/m² | Compound |
|---|---|---|---|
| 2A | 0.43 g II-1 | 0.24 g II-1 | — |
| 2B | 0.43 g II-1 | 0.24 g II-1 | I-8 |
| 2C | 0.32 g II-6 | 0.18 g II-6 | — |
| 2D | 0.32 g II-6 | 0.18 g II-6 | I-10 |
| 2E | 0.27 g II-7 | 0.15 g II-7 | — |
| 2F | 0.27 g II-7 | 0.15 g II-7 | I-15 |
| 2G | 0.30 g II-11 | 0.17 g II-11 | — |
| 2H | 0.30 g II-11 | 0.17 g II-11 | I-20 |
| 2I | 0.50 g II-8 | 0.28 g II-8 | — |
| 2J | 0.50 g II-8 | 0.28 g II-8 | I-18 |
| 2K | 0.54 g II-9 | 0.30 g II-9 | — |
| 2L | 0.54 g II-9 | 0.30 g II-9 | I-11 |

TABLE 3

| Sample | Magenta grain (RMS) at colour density (above fog) of | | |
|---|---|---|---|
| | 0.5 | 1.0 | 1.5 |
| 2A | 13.5 | 12.2 | 11.4 |
| 2B | 10.2 | 9.9 | 9.8 |
| 2C | 14.1 | 13.1 | 11.9 |
| 2D | 11.3 | 10.7 | 10.5 |
| 2E | 14.8 | 13.7 | 12.7 |
| 2F | 12.0 | 11.2 | 10.9 |
| 2G | 14.7 | 13.8 | 12.8 |
| 2H | 12.0 | 11.1 | 10.9 |
| 2I | 14.9 | 14.0 | 13.1 |
| 2J | 12.2 | 11.4 | 11.2 |
| 2K | 13.7 | 12.3 | 11.4 |
| 2L | 10.3 | 10.0 | 9.9 |

The following examples 3A to 3H differ from example 2A in that other couplers with and without additions according to the invention were used in the high sensitivity green-sensitive layer 8. The corresponding combinations may be found in table 4. The compounds according to the invention were each used in a quantity of mol. % relative to the colour couplers.

TABLE 4

| Sample | Magenta coupler in layer 8 | Compound |
|---|---|---|
| 3A | 0.2 g II-4 | — |
| 3B | 0.2 g II-4 | I-3 |
| 3C | 0.3 g II-5 | — |
| 3D | 0.3 g II-5 | I-7 |
| 3E | 0.2 g II-10 | — |
| 3F | 0.2 g II-10 | I-11 |
| 3G | 0.25 g II-11 | — |
| 3H | 0.25 g II-11 | I-28 |

Sample 3B, 3D, 3F and 3H are according to the invention.

After exposure and processing as described in example 1, colour grain values were measured. The values may be found in table 5. The samples according to the invention exhibit considerably lower grain than the comparison tests.

TABLE 5

| Sample | Magenta grain (RMS) at colour density (above fog) of | | |
|---|---|---|---|
| | 0.2 | 0.6 | 1.0 |
| 3A | 15.5 | 13.4 | 13.2 |
| 3B | 12.7 | 10.8 | 10.2 |
| 3C | 14.7 | 12.8 | 12.2 |
| 3D | 12.2 | 10.3 | 10.0 |
| 3E | 15.3 | 13.7 | 13.2 |
| 3F | 12.3 | 10.8 | 10.3 |
| 3G | 16.1 | 12.8 | 11.8 |
| 3H | 13.0 | 11.1 | 10.8 |

Example 4A differs from example 3A in that 60 mol. % of compound I-10 according to the invention were used in addition to coupler II-4 in the high-sensitivity layer 8. Comparison tests 4B to 4F contain comparison compounds instead of compound I-10 according to the invention.

Table 6 below shows the magenta grain values (RMS) at density 0.2 and 0.5 above fog, together with the relative sensitivity and gradation (γ) of the samples.

TABLE 6

| Example | Additional compound | Relative sensitivity | γ | RMS D = 0.2 | RMS D = 0.5 |
|---|---|---|---|---|---|
| 4A | I-10 | 100 | 0.80 | 12.2 | 11.0 |
| 4B | STA | 95 | 0.82 | 15.4 | 13.7 |
| 4C | STB | 59 | 0.45 | 11.8 | 10.9 |
| 4D | STC | 64 | 0.49 | 12.1 | 11.1 |
| 4E | STD | 48 | 0.38 | 11.6 | 10.8 |
| 4F | STE | 100 | 0.78 | 15.6 | 13.8 |
| 4G | STF | 43 | 0.32 | 11.4 | 10.8 |

The results show that compound I-10 according to the invention is superior to the comparison compounds. While the comparison compounds do indeed in some cases have lower colour grain values, their γ values and sensitivity values are then too low, such that they are unusable for a photographic recording material.

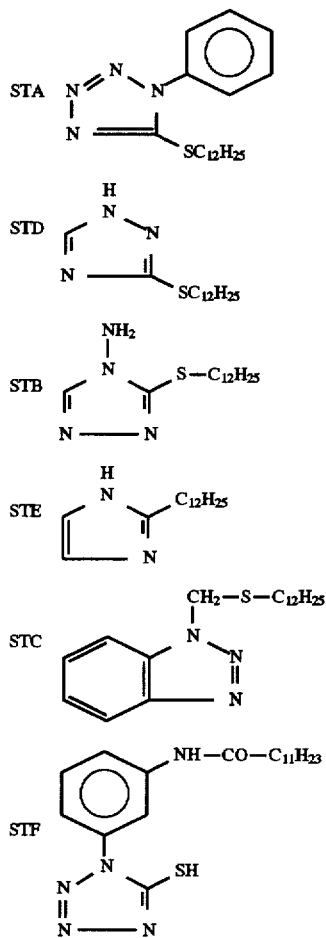

We claim:

1. A color photographic silver halide material which comprises a transparent support, at least one silver halide emulsion layer and at least one non-light sensitive layer applied thereto, wherein the silver halide emulsion layer contains at least one color coupler and a silver halide consisting of 0 to 15 mol-% silver iodide, 0 to 20 mol-% of silver chloride and 65 to 100 mol-% of silver bromide, and wherein the silver emulsion layer or the non-light sensitive layer contains a compound of the formula (I)

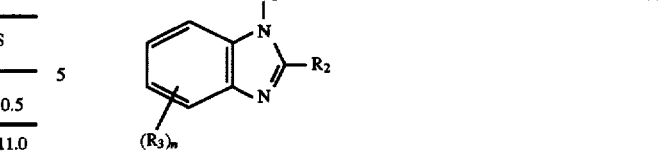

wherein $R_1$ is hydrogen, unsubstituted alkyl having 1 to 20 C atoms or alkyl with 1 to 4 C atoms substituted by hydroxy, phenyl, alkylmercapto or arylmercapto, $R_2$ is unsubstituted saturated or unsaturated alkyl having 1 to 20 C atoms, alkyl having 1 to 4 C atoms substituted by alkylmercapto, cyano or alkoxycarbonyl or is $SR_4$, $R_3$ is alkyl having 1 to 20 C atoms, phenyl or halogen, $R_4$ is alkyl having 1 to 20 C atoms and n is 0, 1 or 2.

2. The color photographic silver halide material according to claim 1, wherein the compound of formula (I) is used in the silver halide emulsion layer.

3. The color photographic silver halide material according to claim 1, wherein the coupler is a 2-equivalent pyrazolone magenta coupler.

4. The color photographic silver halide material according to claim 1, wherein the coupler has a molecular weight of between 500 and 1500 and is used in a quantity of 0.5 to 1.5 g/m² and the compound of the formula (I) is used in a quantity of 50 to 500 mg/m².

5. The color photographic silver halide material according to claim 1, wherein the coupler is a pyrazolone coupler of the formula (II)

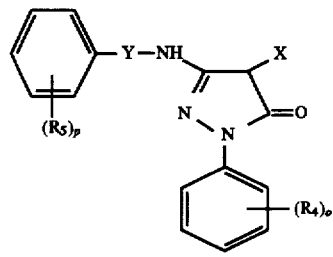

in which each $R_4$ is identical or different and is halogen, CN, alkylsulphonyl, arylsulphonyl, sulphamoyl, sulphamido, carbamoyl, carbonamido, alkoxy, acyloxy, aryloxy, alkoxycarbonyl, ureido, nitro, alkyl or trifluoromethyl, each $R_5$ is identical or different and is the same as defined in $R_4$ or aryl, alkylsulphoxyl, arylsulphoxyl, acyl, imido, carbamato, heteroacylyl, alkylthio, carboxyl or hydroxyl, X is an elimination group, Y is a direct bond or CO and o and p are identical or different and are 0 or a number from 1 to 5.

6. The color photographic silver halide material as claimed in claim 5, wherein o and p are identical or different and are greater than 1.

7. The color photographic silver halide material according to claim 1, wherein the coupler is of the formula (III)

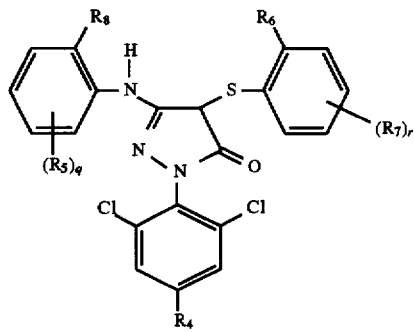
(III)

in which

R$_4$ is halogen, CN, alkylsulphonyl, arylsulphonyl, sulphamoyl, sulphamido, carbamoyl, carbonamido, alkoxy, acyloxyl, aryloxy, alkoxycarbonyl, ureido, nitro, alkyl or trifluoromethyl, each R$_5$ is identical or different and is the same as defined in R$_4$ or aryl, alkylsulphoxyl, arylsulphoxyl, acyl, imido, carbamato, heteroacylyl, alkylthio, carboxyl or hydroxyl, R$_6$ is acylamino or sulphonylamino each R$_7$ is identical or different and is hydrogen or an organic residue, R$_8$ is chlorine or C$_1$–C$_4$ alkoxy, r and q mutually independently of each other are 0, 1 or 2.

8. The color photographic silver halide material according to claim 7, wherein R$_7$ is hydrogen.

9. The color photographic silver halide material according to claim 1, wherein R$_1$ is hydrogen.

10. The color photographic silver halide material according to claim 1, wherein R$_3$ is hydrogen.

11. The color photographic silver halide material according to claim 10, wherein R$_1$ is hydrogen.

12. The color photographic silver halide material according to claim 8, wherein R$_1$ and R$_3$ are hydrogen.

13. A color photographic silver halide material which comprises a support, at least one silver halide emulsion layer and at least one non-light sensitive layer applied thereto, wherein the silver halide emulsion layer contains at least one color coupler, and wherein the silver emulsion layer or the non-light sensitive layer contains a compound selected from the group consisting of:

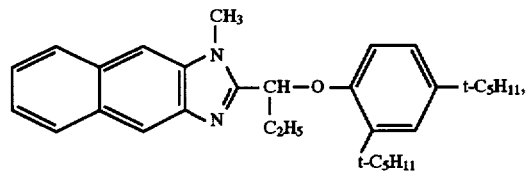

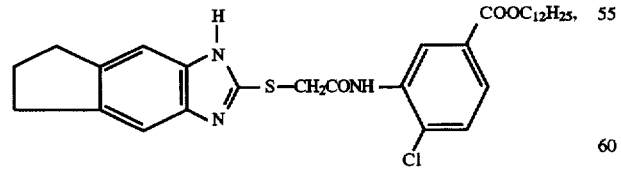

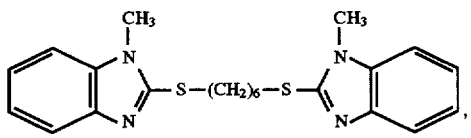

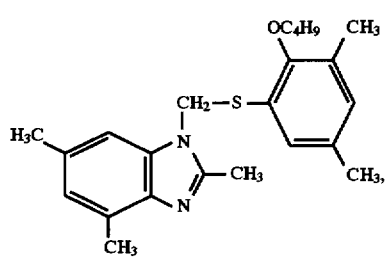

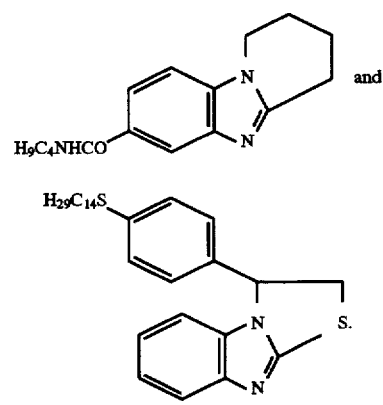

14. A color photographic silver halide material which comprises a support, at least one silver halide emulsion layer and at least one non-light sensitive layer applied thereto, wherein the silver halide emulsion layer contains at least one color coupler, and wherein the silver emulsion layer or the non-light sensitive layer contains a compound of the formula (II)

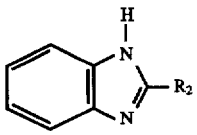
(II)

wherein

R$_2$ is C$_{17}$H$_{33}$, C$_{13}$H$_{27}$, C$_{17}$H$_{31}$, C$_6$H$_{13}$S, C$_8$H$_{17}$S, C$_{10}$H$_{21}$S, C$_{12}$H$_{25}$S, C$_{13}$H$_{27}$S, C$_{14}$H$_{29}$S, C$_{16}$H$_{33}$S, C$_{18}$H$_{37}$S, CH(CH$_3$)CO$_2$C$_{12}$H$_{25}$, CH$_2$CH$_2$SC$_{18}$H$_{37}$, CH$_2$SC$_{12}$H$_{25}$, or 2—C$_{10}$H$_{21}$S-phenyl.

* * * * *